United States Patent
Thyzel

(10) Patent No.: US 11,234,865 B2
(45) Date of Patent: Feb. 1, 2022

(54) METHOD FOR CHANGING THE PERCEPTUAL COLOR APPEARANCE OF THE IRIS OF A HUMAN'S OR ANIMAL'S EYE

(71) Applicant: Reinhardt Thyzel, Eckental (DE)

(72) Inventor: Reinhardt Thyzel, Eckental (DE)

( * ) Notice: Subject to any disclaimer, the term of this patent is extended or adjusted under 35 U.S.C. 154(b) by 68 days.

(21) Appl. No.: 16/340,077

(22) PCT Filed: Sep. 20, 2017

(86) PCT No.: PCT/EP2017/073809
§ 371 (c)(1),
(2) Date: Apr. 5, 2019

(87) PCT Pub. No.: WO2018/069013
PCT Pub. Date: Apr. 19, 2018

(65) Prior Publication Data
US 2020/0046560 A1    Feb. 13, 2020

(30) Foreign Application Priority Data

Oct. 12, 2016  (DE) ..................... 10 2016 119 425.5

(51) Int. Cl.
*A61F 9/008*    (2006.01)

(52) U.S. Cl.
CPC ...... *A61F 9/00827* (2013.01); *A61F 9/00804* (2013.01); *A61F 2009/00844* (2013.01); *A61F 2009/00876* (2013.01); *A61F 2009/00897* (2013.01)

(58) Field of Classification Search
CPC .............. A61F 9/00827; A61F 9/00804; A61F 9/00802; A61F 9/00806; A61F 9/00829; A61F 2009/00844; A61F 2009/00861; A61F 2009/00876; A61F 9/008
See application file for complete search history.

(56) References Cited

U.S. PATENT DOCUMENTS

| 8,206,379 B2 | 6/2012 | Homer |
| 2005/0049584 A1* | 3/2005 | Homer ................ A61F 9/00817 606/33 |
| 2008/0027519 A1* | 1/2008 | Guerrero ................ A61F 9/008 607/89 |

(Continued)

*Primary Examiner* — Allen Porter
*Assistant Examiner* — Skylar Lindsey Christianson
(74) *Attorney, Agent, or Firm* — Workman Nydegger

(57) ABSTRACT

The underlying invention is directed to a method for changing the human perceptual color appearance of the iris of a human's or animal's eye by selectively decreasing the density of pigments of the anterior stroma layer of the iris. The method comprises generating, by a generator module, a plurality of predefined energy quantities; and applying, by the generator module, one or more of the predefined energy quantities to the anterior stroma layer, wherein each of the predefined energy quantities is generated and applied, such that the energy quantities ablate, at least in part, melanocytes of the stroma whilst leaving non-melanocyte tissue of at least the stroma essentially undamaged, and wherein the predefined energy quantities generated and applied to the anterior stroma layer in the form of pressure waves and/or pulses generated within a fluid medium that is in fluidical communication with the anterior stroma layer.

21 Claims, 5 Drawing Sheets

(56) References Cited

U.S. PATENT DOCUMENTS

2009/0118663 A1\* 5/2009 Rockley .............. A61M 1/0076
  604/20
2014/0148737 A1 5/2014 Homer
2017/0035608 A1\* 2/2017 Boxer Wachler ....... A61F 9/008

\* cited by examiner

METHOD FOR CHANGING THE PERCEPTUAL COLOR APPEARANCE OF THE IRIS OF A HUMAN'S OR ANIMAL'S EYE

CROSS-REFERENCE TO RELATED APPLICATIONS

The present invention is a 35 U.S.C. § 371 U.S. National Stage Application corresponding to PCT Application no. PCT/EP2017/073809, filed on Sep. 20, 2017, which claims the benefit of priority to German Patent Application No. DE 10 2016 119 425.5 filed Oct. 12, 2016. The entire content of each of the aforementioned patent applications is incorporated herein by reference.

BACKGROUND OF THE INVENTION

1. Field of the Invention

The invention is related to the field of changing the human perceptual color appearance of the iris of a human's or animal's eye.

2. Background

The iris of the human or animal eye is a thin skin and muscular like tissue that surrounds the pupil and allows the pupil to be opened or closed thereby controlling the amount of light that can enter the inner eye, meaning that the level of dilation or contraction of the iris determines the amount of light that can enter the inner eye.

The pupil and iris separate the anterior eye chamber from the posterior eye chamber, both eye chambers being filled with transparent eye fluid (chamber fluid, aqueous humour) consisting mainly of water.

Behind the pupil and adjacent to the posterior chamber is the eye lens which is positioned within the lens capsule bag suspended by zonular fibres and ciliar muscles for optical accommodation of the lens. Behind the posterior chamber and the lens the vitreous body is situated, that in part is surrounded by the retina. The anterior eye chamber is closed by the cornea as a type of protective shield constituting an anterior wall for the anterior eye chamber.

The colour appearance of the iris as perceived by human beings determines the impression of the eye, and so the colour appearance of the iris is usually referred to as the "colour of the eyes". The colour of the eyes/iris can vary from blue and green to grey and brown and all kind of mixtures in between.

The "colour" of the iris as perceived by humans is generally determined by the density of pigments, i.e. melanin pigments, present on or in the anterior stroma layer of the iris. Apart from the anterior stroma layer, the iris comprises a posterior pigment layer (epithelium pigmentosum) that is located on the back side of the iris, and which is provided for light absorption preventing light from entering the inner eye through the iris.

Provided that the posterior pigmented layer is intact, i.e. contains sufficient pigments, the perceptual color is mainly determined by the density of pigments in the anterior stroma layer of the iris. The lower the density of the pigments in the anterior stroma layer is, the more the perceived eye color is shifted towards blue. Conversely, the higher the density of the pigments in the anterior stroma layer, the darker the color appearance is, ranging from green to brown, and in extreme cases almost black.

For diverse non-therapeutical, and in particular non-surgical reasons, for example aesthetic reasons, which shall not be detailed herein, and which may be induced by social issues, the desire of changing the color appearance of the eyes of a human being or an animal emerged. In particular, the desire of shifting the eye color towards blue emerged, and corresponding methods have been developed in recent years, wherein such methods consider reducing the amount of active melanin pigments in the anterior stroma layer.

When decreasing the density of melanin pigments in the anterior stroma layer, care has to be taken to avoid damaging the fibrovascular tissue layer of the stroma and the posterior pigment layer (epithelium pigmentosum), because such damages could cause functional impairment of the eye.

Therefore, gentle yet efficient procedures are needed for changing the melanin pigment density of the stroma layer.

Document U.S. Pat. No. 8,206,379 B2 describes a method for altering perceived iris color, wherein it is proposed to use a laser beam for irradiating the stroma layer such that either the melanin is destroyed, or such that the pigmented cells, i.e. the melanocytes, of the stroma layer are selectively killed such that they can be removed by metabolic processes. Destroyed melanin or metabolized cells may be removed, involving metabolic processes, via the intraocular fluid over the Schlemm's Canal. Using laser energy for irradiating the stroma layer, however, may involve providing precautionary measures in order to prevent the eye's retina from being irradiated with laser energy.

However, it has been recognized, that removal of the melanocytes or the melanin by means of metabolism may involve a comparatively lengthy process, meaning that the result of a treatment of the stroma layer for changing the color appearance may appear after some time, possibly necessitating further treatments of the stroma layer to finally obtain a blue color appearance of the iris, for example.

BRIEF SUMMARY OF THE INVENTION

In view of this, it is an object of the invention to provide an alternative way for changing the human perceptual color appearance of the iris of a human's or animal's eye. In particular, a way of changing the color appearance shall be provided that is suitable for expeditious and efficient, yet gently changing the color appearance of the iris by changing (in particular: modifying, altering) the density of melanin pigments in the anterior stroma layer of the iris.

These and further objects as described hereinbelow are solved by the features of the independent claims. Embodiments of the invention in particular result from the dependent claims and the exemplary embodiments described in the following detailed description.

Embodiments according to the invention are in particular disclosed in the attached claims directed to a method. However, the claim features and any features described hereinbelow may be used in connection with different claim categories. Further, the dependencies or references back in the attached claims are chosen for formal reasons only. However any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

In embodiments of the invention, a non-therapeutical, in particular non-surgical, method, for changing the human perceptual color appearance of the iris of a human's or animal's eye is provided. The proposed method involves selectively decreasing (in particular: altering, changing, modifying) the density of pigments, specifically melanin pigments, of the anterior stroma layer, in particular the anterior border layer of the stroma layer of the iris of the human's or animal's eye.

The proposed method comprises the steps of generating, by the operation of a generator module, a plurality of predefined energy quantities, and applying (in particular: impinging), by the generator module, one or more of the predefined energy quantities to the anterior stroma layer.

The one or more energy quantities may be applied to the stroma from a location positioned anterior, and/or lateral relative to the iris, for example relative to the optical axis of the eye.

The optical axis of the eye may be oriented essentially horizontally or essentially vertically during application of the energy quantities. In particular, the optical axis of the eye may be oriented vertically such that energy quantities, i.e. pressure pulses (in particular also: pressure waves), may be applied in vertical direction to the stroma, for example via an automated robotic arm positioned at least in part vertically above the eye. It shall be noted, that the energy quantities may also be applied by manual operation or at least partial manual operation, in particular movement, of a corresponding device for generating and applying pressure pulses.

For example, the eye of a person may be impinged with the energy quantities in an arrangement in which the person is lying essentially horizontally on a table or similar in particular such that the optical axis of the eye is oriented essentially vertically, and in which the energy quantities are applied essentially vertically to the stroma layer or at a particular angle from above.

In particular, the one or more energy quantities may be applied to the anterior stroma layer such that an angle of incident as regards a main direction of propagation is essentially constant and/or kept within a predefined range of angles. Further, the one or more energy quantities may be applied such that the density of applied energy at the stroma layer is substantially constant and/or remains within a predefined range of energy density.

The "selective decrease" of the pigment density as proposed with the inventive method in particular shall mean that the energy quantity is generated and applied in such a way that apart from melanocyte tissue, substantially no damage is caused with the eye or parts thereof, such as the retina, cornea and fibrovascular tissue of the stroma.

With the proposed method it is provided that each of the applied energy quantities is generated and applied such that it ablates, i.e. that it is suitable for ablating (in particular: removing, avulsing), upon interacting with the anterior pigmented stroma layer, at least in part, and/or essentially completely melanocytes, i.e. melanin pigment containing cells, of the stroma, in particular of the anterior stroma layer.

The energy quantities are further generated and applied in such a way that non-melanocyte tissue, of for example the stroma, retina and the cornea, and other parts of the eye, are left essentially undamaged. In particular, the one or more energy quantities in embodiments may be generated, in particular focused as regards the energy areal density, such that, melanocyte tissue is ablated whilst non-melanocyte tissue remains substantially unaffected.

The specificity for being able to ablate the melanocytes may be obtained by adequately setting or selecting the energy, power, power density, in particular surface power density, the application duration, angle of incident, focusing angle, and other parameters related to the generation and/or application of the energy quantities.

Specificity may also be obtained by generating and applying the energy quantities in a particular pulsed form, wherein respective pulse lengths of the pulsed energy quantities may be selected so as to obtain specific ablation of melanocytes. For example, a particular pulse length (e.g. 4 ns) and pulse energy (e.g. 2 mJ) may be selected.

With the proposed method, the predefined energy quantities are generated and applied to the anterior stroma layer in the form of pressure waves or pressure pulses generated within a fluid medium that is in fluidical communication with the anterior stroma layer, in particular in fluidical communication with the anterior eye chamber that in turn is in fluidical communication with the anterior stroma layer.

The proposed method of generating and applying the pressure pulses so as to obtain ablation and discharge into the anterior eye chamber has the advantage, that the fibrovascular tissue of the stroma may be freed comparatively expeditious, quickly, and/or efficiently from melanocytes and melanin pigment contained therein. Beyond that, using pressure pulses is considered as a comparatively gentle way for removing melanocyte tissue, in particular gentle as regards possible retina damages. Thus the effects and results of applying the method to the stroma layer of the iris may become readily apparent, which may contribute to shorten the overall duration for obtaining the desired change in the color appearance of the iris.

Beyond that, generating and applying the energy quantities as proposed above, i.e. by pressure pulses such that the ablated melanocytes are discharged into the anterior eye chamber, may also be advantageous for reducing the risk of applying further energy quantities to surface areas of the stroma that already have been sufficiently impinged with pressure pulses, which may for example be the case with the known prior art methods.

In embodiments, the energy quantities may at least in part be generated and applied in such a way that ablated tissue debris, and/or pigment debris of the ablated melanocytes, that is generated as an immediate (in particular: direct) cause (in particular: response) of one or more of the applied energy quantities, is, at least in part, discharged (in particular: purged) into the anterior eye chamber (in particular: the chamber between the anterior layer of the iris and the posterior endothelial layer of the cornea of the eye), such that the discharged tissue/cell debris can be removed (in particular: flushed away) by a mechanically generated (in particular: artificial—in contrast to physical/natural/by medication) flow of rinsing solution through or within the anterior eye chamber. In view of this, the proposed method may comprise a step of generating and/or maintaining a flow or rinsing solution through of within the anterior eye chamber, the flow of rinsing solution generated such that discharged (in particular: ablated) melanocyte tissue may be removed (in particular: carried away) from the anterior eye chamber.

Removing the ablated melanocyte material/tissue may avoid that generated pressure pulses are distorted and/or impaired, for example in that ablated melanocyte tissue at least in part absorbs and/or scatters incident pressure pulses. Removal of the ablated melanocyte tissue as proposed, for example by the mechanical flow maintained at least during a phase covering the impingement of pressure pulses, may contribute to enhanced specificity of ablation.

In embodiments, at least some of the applied pressure pulses, for example substantially all of the applied and/or generated pressure pulses, comprise a pressure current and/or a pressure wave and/or a shock wave propagating, after generation, in the fluid medium. The pressure pulse(s) may have a particular preferential direction (in particular also: main propagation direction) directed towards the anterior stroma layer. Pressure pulses, in particular directed pressure pulses have been shown to be efficient for gently ablating melanocyte tissue.

In embodiments, at least some of the applied pressure pulses, in particular all of the applied and/or generated pressure pulses, involve a pressure jet of fluid medium, wherein the pressure jet of fluid is generated within the anterior eye chamber. The pressure jet of fluid may be directed under a particular angle of incident towards the anterior stroma layer.

In embodiments, at least some of the pressure pulses, preferably substantially all of the pressure pulses may be generated to induce a local pressure increase within the fluid medium, the pressure increase lying between 50 bar and 1,000 bar, wherein the local pressure increase may prevail within a distance of 0.3 to 0.7 mm, in particular 0.5 mm, from a point of origin of the pressure pulse.

In embodiments, the pressure increase may prevail within and/or may be confined to a cross-sectional area of 0.1 $mm^2$ to 12 $mm^2$ measured in a plane substantially perpendicular to the main propagation direction at a distance of about 5 mm from the point of origin of the pressure pulse.

The parameters as discussed beforehand in connection with the generation of the pressure pulses have shown to be of particular benefit for ablating melanocyte tissue so as to be able to immediately discharge the ablated melanocyte tissue in or with a stream of rinsing solution.

In embodiments, the pressure pulses may be generated by a shock wave generator device. In particular the underlying invention is based on the fact that melanocyte tissue ablation as intended with the present invention can be efficiently obtained by applying shock waves, for example generated as plasma-induced pressure pulses and/or laser-induced cavitation. In particular, it has been found out that the fibrovascular layer or tissue of the stroma is sufficiently strong and/or elastic such that selective ablation of melanocyte tissue is possible by pressure waves/pulses, the ablation of melanocyte tissue decreasing the melanin density of the anterior stroma layer leading to a change in the perceived eye color towards a more blueish shade or hue.

In embodiments, at least one pulse-output region (in particular also: pulse-output surface, orifice, opening) of the shock wave generator device, whilst facing the iris, is moved relative to the anterior stroma layer. The movement of the pulse-output region, i.e. pulse output, may be such that an essentially constant distance to the anterior stroma layer, i.e. a substantially constant distance between the output region and the anterior stroma layer is obtained or prevails.

In embodiments, the method may involve moving the pulse-output region such that the relative movement of the pulse-output region is a continuous movement, for example involving movements at constant speed at least over a predetermined pathway.

In embodiments, the method may involve moving the pulse-output region such that the relative movement of the pulse-output region is a dis-continuous movement, for example targeting predetermined local target regions, for example according to a predetermined sequence of target regions. The dis-continuous movement may involve an intermittent generation of pressure pulses, wherein the intermittent generation of pressure may be synchronized with the discontinuous movement. Dis-continuous and continuous movement may be used in subsequent phases, for example depending on the particular region if the iris processed by pressure pulses in order to ablate the melanocytes.

In embodiments, the method may involve the steps of positioning the pressure-output region at a predetermined, particular target location, and, in particular in case that the steps are carried out subsequently as soon as or after occupying the target location, generating and applying one or more pressure pulses to the target location. Dis-continuous movement and/or application of the pressure pulses may be applied in order to reduce the total surface energy applied to the anterior stroma layer within a particular time period.

The pulse-output region may comprise, as already mentioned, an orifice or opening through which pressure pulses, in particular shock waves and/or pressure jets, may be outputted, emitted or discharged from an inner chamber of the device into the anterior eye chamber and/or the fluid medium. The pressure-output region may comprise or be formed like a type of nozzle. The output region may be implemented and/or formed so as to enable the generation of pressure pulses with a particular, in particular predefined, preferential direction relative to the pulse-output region.

In embodiments, the pulse-output region may be provided at a distal end of an applicator element. The applicator element may be a handheld applicator element, or be implemented for being handled with a robotic arm. The applicator element may in embodiments comprise a needle-shaped extension, in particular, a section of the applicator element may be implemented as a type of needle for insertion into the anterior eye chamber, for example through a hole provided in the cornea of the eye.

In embodiments, the pulse-output region of the applicator element may be provided at a distal end of the needle-shaped extension, for example such that the pulse-output region can be placed and moved by correspondingly moving the extension, at/or along a predefined path past the anterior stroma layer.

The pulse-output region may be defined by or at an opening at the distal end of the extension. The opening may be provided and defined such that the opening plane of the opening is tilted at a predefined angle to the longitudinal axis of the extension. The opening may lead to and/or fluidically be connected with a channel or cavity, in particular inner channel/cavity, of the applicator device such that pressure pulses generated within the inner channel or cavity, for example by laser-induced plasma generation, may exit the chamber/cavity and propagate from the applicator device with, e.g. a predefined preferential direction, wherein the preferential direction may be tilted by a predefined angle to the longitudinal axis of the applicator, in particular the extension.

In embodiments, the pressure pulses may be generated with a defined, in particular constant or constantly varying, pulse repetition rate. The pulse repetition rate may for example be adjustable within a pre-specified range by a user via a user interface. Further, in embodiments, the pulse repetition rate of the pressure pulses may lie in the range of 1 pulse per second to 10 pulses per second, in particular 10 or 4 or 2 or 1 pulses per second.

In embodiments, the pressure pulses may be generated by means of at least one pressure-pulse generator unit of a pressure-pulse generator. The method may further involve a step of fluidically coupling and/or maintaining a fluidical communication between the pressure-pulse generator unit and the fluid medium within the anterior eye chamber. The one pressure-pulse generator may for example be operated to generate, within the fluid medium, or a fluid that is in fluidical communication or contact with the fluid medium a plasma such that at least one plasma-induced pressure pulse is generated within and/or discharged into the fluid medium.

In embodiments, the method may further comprise a step of irradiating a laser target material with laser irradiation thereby generating a shock wave inducing one or more than one pressure pulses by optical breakdown caused by laser energy being absorbed at the target material and/or laser-induced cavitation within the fluid medium.

The irradiating of the laser target may in embodiments comprise a step of generating and applying one or more laser pulses to the laser target material, wherein the one or more laser pulses may be generated such that they have a pulse duration lying between 5 ns and 20 ns, preferably between 8 ns to 12 ns, and/or such that they have a pulse energy between 1 and 20 mJ, preferably between 6 and 15 mJ. The one or more laser pulses may be generated and applied to the target laser material in such a way that each laser pulse generates at least one pressure pulse, in particular such that each laser pulse generates or induces only one pressure pulse.

In embodiments, the method may involve that a triggering event for the pressure pulse is generated, for example by means of a plasma that is induced by optical breakdown and/or by laser-induced cavitation, in an inner channel of a pressure pulse applicator.

The inner channel may be filled and/or flushed with fluid medium and/or rinsing solution or a fluid similarly compatible with intraocular humoral. The method may involve establishing a fluid communication between the inner chamber and the anterior eye chamber such that a generated pressure pulse may propagate from the source of origin via at least a part of the channel through a distal exit opening of the applicator and applied to the target location at the anterior stroma layer. For example, a laser pulse may be applied to a laser target material that is placed within the inner channel, wherein the laser pulse is applied to the target material such that by optical breakdown of the applied laser energy a plasma is generated in the liquid in the inner chamber, wherein the plasma that in turn gives rise to a pressure pulse within the liquid, propagating into a defined direction of propagation. The defined direction of propagation may be determined by the shape of the inner channel, the shape and/or orientation of the laser target material, the laser pulse spot size, the laser spot shape, the shape, form and/or orientation of a distal opening defining a pulse-output region, and others.

In embodiments of the method, the source of origin, i.e. the source of origin of the pressure pulse, for example the location where the plasma and/or cavitation is generated, may be located at a laser target, in particular laser target material, provided at an inner wall of the inner channel. The laser target may be provided at a distal end of the cavity close to the exit opening. A triggering event for generating or inducing the pressure pulse may be generated by irradiating the laser target with a defined laser energy so as to generate the one or more pressure pulses by means of an optical breakdown-induced plasma within the inner channel and/or laser-induced cavitation.

In embodiments, the method may involve a step of applying the laser energy to the laser target material by means of or through an optical system including an optical fiber that least in part runs or is guided within the inner cavity. The optical fiber may be configured and positioned such that a free end of the optical fiber is positioned opposite to the laser target material such that laser radiation, in particular laser pulses, exiting the optical fiber is/are directed towards and impinge the laser target.

In embodiments, the method may involve a step of generating and/or maintaining a supply flow of fluid medium and/or rinsing solution through the inner channel into the anterior eye chamber, and a step of generating and/or maintaining a discharge flow of fluid medium and/or rising solution out of the anterior eye chamber through a drain tube. The drain tube may be configured and positioned in such a way that it is fluidically connected with the anterior eye chamber and enables discharging fluid medium and/or rinsing solution out of the anterior eye chamber. The drain tube may be separate from an applicator implementing the inner chamber. However, the drain tube may be part, in particular integral part, of an applicator implementing the inner chamber. The drain tube and/or a corresponding drain element may in embodiments comprise a filter element for filtering out melanocyte cell debris from the liquid passing through. In particular in this way, a circular flow of rinsing medium through the inner channel, the drain and filter element may be obtained and/or used for generating a flow for removing ablated melanocyte tissue. The filter element may for example be implemented with the applicator, in particular as an integral part.

The supply flow and discharge flow may be generated in such a way that the mean intraocular pressure in the anterior eye chamber is or remains substantially constant while carrying out the method. For example, the intraocular pressure may be kept substantially constant at a value lying in the range between 16 mmHg and 20 mmHg.

In embodiments, the supply and discharge flow of fluid medium and/or rinsing solution is generated and/or maintained such that tissue and/or pigment debris generated by melanocyte ablation induced by impinging pressure pulses, i.e. pressure-pulsed melanocyte ablation, is or can be removed from the anterior eye chamber via the discharge flow.

As already indicated, the drain tube, which may be implemented as a discharge channel for example, may, at least in part, be implemented as a further inner channel of the applicator element, for example running in parallel to the inner channel that accommodates the laser target material. Thus, the discharge flow may be obtained by using a single applicator element, easing execution of the proposed method.

In embodiments, the method may comprise a step of maintaining the supply and discharge flow for a respectively predetermined lapse of time at least during, and/or after applying the one or more pressure pulses to the anterior stroma layer.

In embodiments, the method may involve maintaining the supply and discharge flow during a predefined lapse of time prior to applying the one or more pressure pulses to the anterior stroma layer.

Further embodiments may involve maintaining the supply and discharge flow for at least one predetermined lapse of time in accordance with a respective, predetermined flow rate profile. The predetermined flow rate profile may be constant over time, at least for one, optionally for each, lapse of time. In embodiments, at least one of a start and end point of at least one lapse of time may be triggered by the generating, and/or applying the predefined pressure pulse.

In embodiments, the supply and discharge flow may comprise, at least during a predetermined first period of time, a laminar flow, and/or at least during a predetermined second period of time a turbulent flow.

In embodiments, the method may comprise the step of partitioning, for example via a partitioning module, such as for example on the basis of a captured image of the iris, at least a part of the surface area of the anterior stroma layer into a number of predefined surface sections. The surface sections may have a predetermined size and/or predetermined location and/or distribution on the anterior stroma layer. A respective number of pressure pulses may be applied to one or more surface sections of the anterior stroma layer.

The pressure pulses may be applied to respective surface areas of the anterior stroma layer in accordance with a predefined scheme, wherein the predefined scheme may comprise a pre-set path or pathway, or a pre-defined sequence of pre-defined locations on or along the anterior stroma layer. The number and sequence of surface areas may be selected and/or defined in such a way that the whole pigmented area of the anterior stroma layer is impinged at least once with one or more pressure pulses while carrying out the method.

As already indicated, the predefined surface sections and/or the pathway may be processed in accordance with a predefined succession of surface sections, in particular surface locations. The predefined succession may for example be determined by the partitioning module, and/or may be determined based at least in part on the pigment density of the iris, the intended degree of pigment removal, iris size and shape and other parameters, which parameters may also be used for setting the pulse energy and other operational settings.

In embodiments, the method may involve that the predetermined surface sections, in particular the size of one or more of the predetermined surface sections, and/or the particular succession of surface sections within the processing sequence and/or the pathway for processing the anterior stroma layer, in particular a pathway of successive target locations, and/or the energy content and/or power of the pulse(s) are determined on the basis of the density of pigments, and/or the specific location of the surface area on the iris and/or the overall size of the iris.

In embodiments, the method may involve that at least one parameter of the mechanically generated flow is determined on the basis of the specific location of a respectively processed surface section and/or pathway (in particular: route), the particular succession of the surface sections, the density of pigments, the size of a respective surface section, and/or one or more than one parameter related to generating and/or applying the energy quantities.

In embodiments, the method may comprise tracking, by a tracking module, in particular an optical tracking module, one or more than one of a position, shape, and movement of the eye or one of the components of the eye, such as the iris, the pupil and/or the eyelid, for example relative to a spatial reference point. The method may further comprise applying, at least in part, the pressure pulses, optionally each of the pressure pulses, in dependence on the tracking result.

The tracking result, i.e. the outcome of the tracking procedure, may for example comprise a determination indicating whether or not the location, and/or size of the iris or pupil has changed, and/or whether or not the eye/iris has (been) moved.

In embodiments, the method may comprise a step of inhibiting the generator module and/or inhibiting application of pressure pulses in case that the tracking result indicates one or more of a change in position, a change in location, a change in shape, and movement of the eye or of at least one component of the eye. In embodiments, the method may comprise relocating a target setting for the pressure pulse in accordance with one or more of a change in position, a change in location, a change in shape, and a movement of the eye or at least one component of the eye.

Tracking in particular has the advantage that the iris or other parts of the eye, such as for example the lens, may be impaired or even damaged by for example falsely applying an energy quantity due to eye movement going along with iris movement. Adequately operating the tracking module in particular may contribute to overall safety, in particular in cases where trained medical staff conducts the method of changing eye color. Further, tracking is suitable and helpful for automating or at least semi-automating the proposed method for changing eye color.

For tracking the eye/iris movement in a method or system for changing the eye color, an eye tracker using a stereoscopic camera system, in particular in connection with infrared light, may be used. The eye tracker may be configured to operate independently from ambient light, or may require specific illumination. The exe tracker, in particular the eye tracking, may involve determining 3D-position of pupil or iris, 3D-viewing direction, pupil size, viewing focus relative to a predefined surface/object.

Embodiments of the method may involve scanning, for example by using a scanning module, at least the iris or sections thereof, and/or the anterior eye chamber at least during application of the pressure pulses, and storing the scanning result after each predetermined number of applied pressure pulses, and/or determining, based on the scanning result, an actual location of impingement or an actual averaged location of impingement respectively indicating an actual location on the anterior stroma layer/the iris where one or more pressure pulses indeed impinged on the anterior stroma layer, tracking the target locations of impingement, and/or controlling, based on the scanning result, the flow of fluid medium and/or rinsing solution within or through the anterior eye chamber, based on the scanning result.

In embodiments, the scanning result may be used to determine a shape of the iris and/or a track, pathway and/or succession of target points to be impinged with the pressure pulses. This may be helpful for automating melanocyte ablation.

The method may further involve a step of determining a density of pigments, in particular a local density of pigments, in particular a pigment profile, or at least a parameter representative of the density, in particular the local density, of pigments based on the scanning result, wherein the generation and/or application of one or more of the pressure pulses may be based at least in part on the determined density of pigments or a corresponding parameter.

In embodiments, the scanning result may be used to determine a change, in particular local change, in the density of pigments, or at least a parameter representative of the change in density of pigments in the anterior stroma layer, wherein the generation and/or application of the pressure pulses may be based on the determined change of the density of pigments or the respective parameter. In particular, ablation of melanocyte issue may be automated or at least semi-automated by using a scanning result of the iris as an input for applying pressure pulses to the iris.

In embodiments, the method may involve generating, based on the scanning result obtained by scanning the iris, one or more than one display objects for display on a display screen to, for example, an operator executing the method. The one or more objects may for example relate to an image of the iris, the image indicating a change of eye color, and/or particular locations of the iris where pressure pulses have been applied. The display objects may be displayed on a screen for presentation to the operator or other persons.

In embodiments, the method may involve the step of providing for display on the display screen operational parameters related to the execution of the method. The displayed parameter(s) may be selected from the group comprising: one or more than one parameter related to the pressure pulses, one or more points of impact of one or more applied pressure pulses on the anterior stroma layer, one or more of a one or more past and future points of impact, of pressure pulses, a first indication representative of a change, in particular local change, of the density of pigments, and a second indication representative of processed, and/or unprocessed surface areas of the anterior surface of the stroma layer. Providing such operational parameters may bring about improvements related to the execution of the method and/or to operational security.

In embodiments, it is proposed to use a method as described herein in connection with any embodiment of the invention in a non-surgical treatment of the iris of an eye of a human being or an animal, the treatment modifying the perceived color of the iris by selectively decreasing the density of melanin pigments of the anterior stroma layer of the eye.

Further embodiments are related to a computer-readable non-transitory storage medium or controller-unit comprising executable instructions which, when executed on a computer or controller-unit cause the computer or controller-unit to execute a method according to one or more embodiments as described herein in connection with the present invention.

In embodiments, the pressure pulse may be applied to the anterior stroma layer by means of a focusing device that is adapted to and set up for focusing (in particular: directing) the generated pressure pulse(s) towards (in particular: onto) a particular location of the anterior stroma layer of the iris of the eye.

In embodiments, the method may involve using a fluid pumping module adapted to and set up for the generation and maintenance of the predefined mechanical (in particular: artificial) flow of fluid medium and/or rinsing solution through and/or within the anterior eye chamber.

The fluid pumping module may be adapted and set up for generating a flow of 15-20 ml/min, and/or for generating a flow in such a way to maintain an inner eye pressure lying in the range between 16 mmHg, i.e. about 21.33 mbar, and 20 mmHg, i.e. about 26.66 mbar.

The method may involve operating a controller unit, i.e. one or more than one controller units, that is/are programmed and set up for carrying out a method according to the invention as proposed and described in any embodiment herein. Specifically, the controller unit may be programmed and set up for carrying out the method according to the invention as described above, including any variation of the method in accordance with all the embodiments and combinations thereof as described herein.

In embodiments, the method as proposed herein may involve operating (in particular: controlling) the energy source, in particular pressure pulse source, and/or focusing device so as to apply (in particular: impinge) the generated predefined pressure pulses, at least in part, to a predefined, in particular melanin-loaded, location (in particular: area) of the anterior layer of the stroma such that melanocyte tissue of the stroma that is impinged with the pressure pulses is ablated (in particular: removed, avulsed) in such a way that it is discharged into the anterior eye chamber, i.e. into the fluid present in the anterior eye chamber, wherein the pressure pulse is applied in such a way that the discharge is a direct cause of the interaction between the energy quantities (in particular: at least one energy quantity) and the tissue.

In embodiments, the method may comprise operating (in particular: controlling) the fluid pumping module so as to maintain the predefined flow over a lapse of time during, and/or a lapse of time directly after applying (in particular: impinging) the pressure pulse to the stroma, such that discharged melanocyte material (in particular: melanocyte debris, melanocyte material, melanin or melanin debris) at least in part may be fluidly discharged from the anterior eye chamber.

The underlying invention in particular has the advantage, that, in a method for changing (in particular: altering) the perceptual iris color of a human's or animal's eye, melanocyte tissue, and thereby melanin pigment, can be efficiently, and within a comparatively short time of application, removed from the stroma, in particular reducing the overall time needed for changing the iris/eye color, and/or reducing the need for prolonged, and/or repeated sessions for pigment removal. Beyond that, the proposed method involving the use of pressure pulses, in particular in combination with a discharge flow for removing the ablated melanocyte tissue material, enables gentle removal of the melanocytes and melanin pigments from the anterior stroma layer.

Maintaining the flow of rinsing solution, which may for example comprise balanced salt solution (BSS) or ringer solution, may support ablation of melanocyte tissue by virtue of the flow of rinsing solution generated through/within the anterior eye chamber.

Removing tissue/tissue debris by way of the maintained flow of rinsing solution, in particular by irrigation, such as for example continued irrigation, has the advantage that it is not necessary to remove all of the necrotic melanocyte tissue generated by applying the energy quantities to the stroma layer by metabolic processes from the anterior eye chamber. This in particular may be advantageous because the Schlemm's Canal, which is the natural pathway where eye humoral may exit the eye chamber, may be impaired, in particular clogged, in case that a comparatively large amount of tissue would have to be precipitated via the Schlemm's Canal. Clogging or partial clogging of the Schlemm's Canal may lead to increased intraocular pressure, which in turn might lead to eye damages on the long term.

The flow rate profile of the flow may follow a particular temporal path, wherein the flow rate profile may for example correspond to a continuous profile, and/or to a step profile.

Regarding the flow rate profile, parameters such as the energy, power, pulse rate by which the pressure pulses are applied to the anterior stroma layer, and others may be used as a basis for adjusting (in particular: setting) a corresponding, in particular suitable, flow rate, i.e. a corresponding flow rate profile. By this, flow-based precipitation and ablation of the melanocyte tissue may be correlated thereby improving the overall efficiency of the proposed method.

In embodiments, at least one of a start and end point of at least one lapse of time being triggered by (in particular: synchronized with) the step of generating, and/or applying the predefined quantity of energy, in particular a pressure pulse. The trigger may involve a lead time assigned to the start of the flow of rinsing solution, wherein the stop time may be set so as to follow-up the end of applying the pressure pulses to the stroma layer.

The mechanical pressure waves, in particular pressure pulses, as proposed herein for ablating the melanocyte tissue may for example be induced (in particular: generated) by, for example laser-induced, cavitation and/or by, for example laser-induced, plasma bursts within the fluid medium, or a fluid that is in fluidical communication with the fluid medium within the anterior eye chamber. It shall be noted that other ways than using a laser for generating the pressure wave/pulse may be used.

Further, the mechanical pressure waves may be directly induced by a plasma burst or blast, and/or by optical breakdown of one or more electromagnetic wave pulses, generated within liquid contained in, or liquid that is in direct fluidical communication with the anterior eye chamber, specifically a fluid contained in the anterior eye chamber.

In embodiments, as already discussed hereinabove, the at least one or more of the energy quantities may be generated as mechanic wave pulses as a direct cause of a plasma-induced burst pulse. The burst pulse may for example be generated by direct interaction of an electromagnetic wave pulse, such as a laser pulse with a laser target, such for example a solid state material, e.g. titanium, that is in fluidical communication with the intraocular humoral.

In embodiments, the plasma-induced burst pulse may be generated at least in part by direct interaction of a corresponding electromagnetic wave pulse, i.e. laser pulse, with a laser target material and/or rinsing-solution in fluidical communication with the anterior eye chamber.

In embodiments, generating the energy quantities may involve operating or adjusting an optical system of the laser device such that a pulsed laser beam for generating at least one or more than one, in particular substantially all, of the pressure pulses is generated, by optical or laser-induced breakdown and/or laser-induced cavitation.

In embodiments, laser pulses for generating the pressure pulses by laser-induced optical breakdown and/or laser-induced cavitation, may be guided from a laser source towards the intended target, at least in part, via at least one fiber optical system. In particular, the laser pulses may be guided from a corresponding laser emitter to an optical system implemented and provided for applying, in particular focusing, the laser pulses to the laser target material and/or to fluid medium in fluidly communication with the anterior eye chamber. Using such a fiber optical system including for example a flexible optical fiber, has the advantage that the optical axis of the eye to be impinged with the laser pulses may be orientated comparatively freely with respect to the laser emitter and corresponding system. In embodiments, the optical axis of the eye may, according to respective preferences, be oriented vertically or horizontally, or according to any other direction respectively suitable for ablating melanocyte pigment from the anterior stroma layer.

A corresponding fiber optical system that can be used when performing the method may comprise an optical fiber having a fiber-optic core diameter lying in the range between 270 µm and 290 µm, in particular at about 280 µm.

In embodiments, the tracking result may not only be used for inhibiting the application (in particular: the release) of one or more of the pressure pulses or pressure waves. The tracking result, which may in embodiments involve a continuous tracking of the eye or a corresponding, suitable component of the eye, e.g. the iris or the pupil, may also and/or in the alternative be used for target control. In particular, the target setting of the pressure pulse may, for target control, be defined and/or relocated in accordance with the tracking result. In particular, the target setting of the energy quantity may, for target control, be relocated in accordance with one or more of a change in position, a change in location, a change in shape, and a movement.

Target control in particular shall mean that the tracking result may be used for controlling for example the generator module, or other suitable module, such that the released pressure pulse is applied to the correct (in particular: intended) target point (in particular: target area) of the anterior stroma layer. By this, the target setting for the one or more pressure waves/pulses may be moved (in particular: adjusted) in accordance with (in particular: synchronously with) a detected eye movement, and/or a detected change in position, location, and/or shape.

Target control may involve positioning an applicator element, in particular a pressure pulse output region, e.g. a pulse output opening, at a particular target point or target area of the anterior stroma layer, and applying the pressure pulse to the anterior stroma layer at the target point or area. The pulse applicator, in particular pulse output region, element, may be moved between a plurality of target points according to particular pattern. The particular pattern may involve repeatedly selecting or determining one or more target points of a plurality of target points. A determined or selected target point may have, in a direction substantially parallel to the anterior stroma layer of the iris, a predefined minimum distance from a previous target point, or substantially adjoin or be adjacent to a previous target point, wherein a first or initial target point may be pre-set or selected randomly, for example.

In embodiments, the succession of target points may be selected/determined such that the target points are arranged along a pre-determined, in particular continuous, pathway running along the anterior stroma layer.

The eye tracking-based target setting control may be implemented such that inhibition of applying the pressure pulse and/or relocation of the target point/area are performed (only) in instances in which the target setting lies outside of the stroma area intended for being treated for color change purposes, and/or in case that the target setting differs from the actual target point/area by more than a predetermined threshold.

Providing such tracking options and controls, in particular by adequately synchronising target setting with eye movement and/or with corresponding changes in or of the eye/iris, may improve execution of the method, and may contribute to enhanced safety in particular with regard to possible damages to non-melanocyte tissue.

In embodiments, scanning results carried out during execution of the method may comprise or involve a representation of the eye chamber(s) and/or the iris, in particular the anterior stroma layer. A corresponding scanning result may be transformed into a parameterized model of the eye/iris/anterior stroma layer, wherein the scanning result, in particular the parameterized model, may be used for target determination, and may be used for (in particular: as the basis of) target tracking, in case that a tracking module is present and used.

The scanning result may in embodiments be stored, for example after a predetermined number of applied energy quantities, e.g. after finalizing method and/or after certain phases, in a non-volatile memory. Such scanning results may be used as documentary evidence for the course of events and/or as an operational history for the procedure of changing the eye/iris color.

In embodiments, the scanning result of the scanning module may be utilized for target setting, in particular for determining (in particular: calculating) a target location, i.e. target location of impingement, or an averaged location of impingement respectively indicating an actual location on the anterior stroma layer or the iris where one or more of the pressure pulses indeed impinged on the anterior stroma layer. When using such a functionality, the target locations of impingement may be tracked, and the tracking result may be stored in a database, for example together with operational parameters related to the generation and application of the energy quantity or quantities.

In embodiments, the flow of rinsing solution within or through the anterior eye chamber may be controlled on the basis of the scanning result.

In embodiments, the density of pigments, in particular the local density of pigments such as for example a pigment profile/distribution, at least, however, a parameter representative of the density/local density of pigments may be determined (in particular: calculated) based on the scanning result.

The determined density of pigments, in particular local density of pigments, the pigment profile and/or the pigment distribution may be used for controlling the generation and/or application, for example along a particular pathway, of one or more of the pressure pulses to the anterior stroma layer. In particular, the determined density of pigments, in particular local density of pigments, the pigment profile and/or the pigment distribution may be used as a parameter for determining (in particular: setting) specificities of the predetermined pressure pulses.

For example, energy, pulse-length, irradiance, and other parameters of for example of a corresponding pressure pulse or wave, may be set at least on part on the basis of the density of pigments, the pigment profile, and/or distribution. Scanning a corresponding section of the eye/iris may be conducted immediately prior to applying a corresponding energy quantity and/or during and/or after applying pressure pulses to the anterior stroma layer of the iris.

In embodiments, it may be provided, that, based on the scanning result, a change, in particular a local change, in the density of pigments, at least, however, a parameter representative of a change/local change in the density of pigments of the anterior stroma layer may be determined (in particular: calculated). Based on such determination the generation and/or application of one or more of the pressure pulses may be controlled based on the determined change/local change in the density of pigments, or a respective parameter representative of a change/local change in the density of pigments.

In embodiments, the method may involve operating a pressure wave generator, wherein the pressure wave generator may be implemented for (in particular: set up for) being operated to generate energy quantities in the form of mechanical pressure waves (in particular: shock waves, blast waves) towards and onto the anterior stroma layer so as to change (in particular: alter, modify) the density of pigments of the anterior stroma layer by ablating melanocyte cells and discharging them into the anterior eye chamber.

The pressure wave generator may in embodiments be operable (in particular: implemented or set up) to generate the pressure waves by, e.g. laser induced, cavitation and/or, e.g. laser-induced, plasma bursts within a liquid that at least is in liquid contact with the eye liquid as contained in the anterior eye chamber.

As has been shown, the underlying invention and embodiments thereof are suitable for changing the human perceptual color appearance of the iris of a human's or animal's eye in an expedient, gentle, and efficient way.

BRIEF DESCRIPTION OF THE DRAWINGS

Exemplary embodiments of the invention will now be described in connection with the annexed figures, in which.

DETAILED DESCRIPTION OF THE PREFERRED EMBODIMENTS

Figure 1:
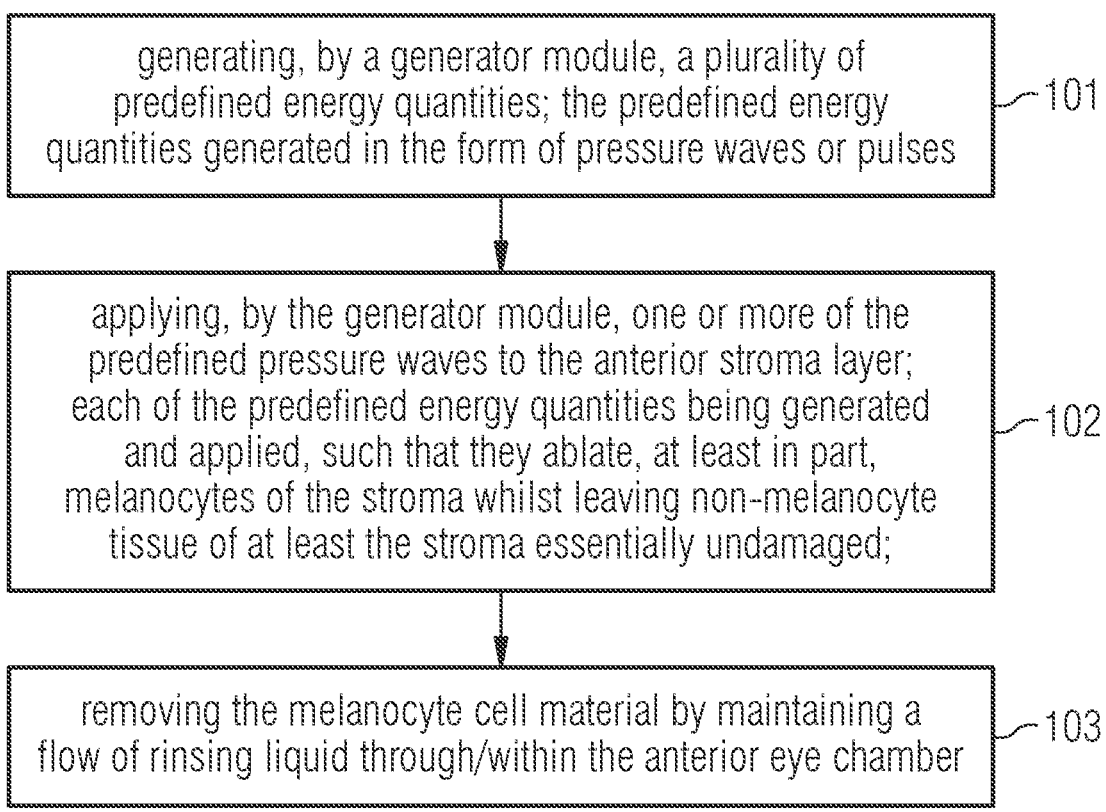
FIG. 1 shows an example flow chart for carrying out an exemplary method according to an embodiment of the invention.

In FIG. 1, an example flow chart for carrying out an exemplary method according to an embodiment of the invention is shown. The method may involve a step of generating 101 by a generator module, in particular by an applicator device 1 as shown in FIG. 2, a plurality of predefined energy quantities 2, wherein the predefined energy quantities 2 are generated in the form of pressure pulses 2, which are shown and depicted in the enlarged view of FIG. 3.

Figure 2:
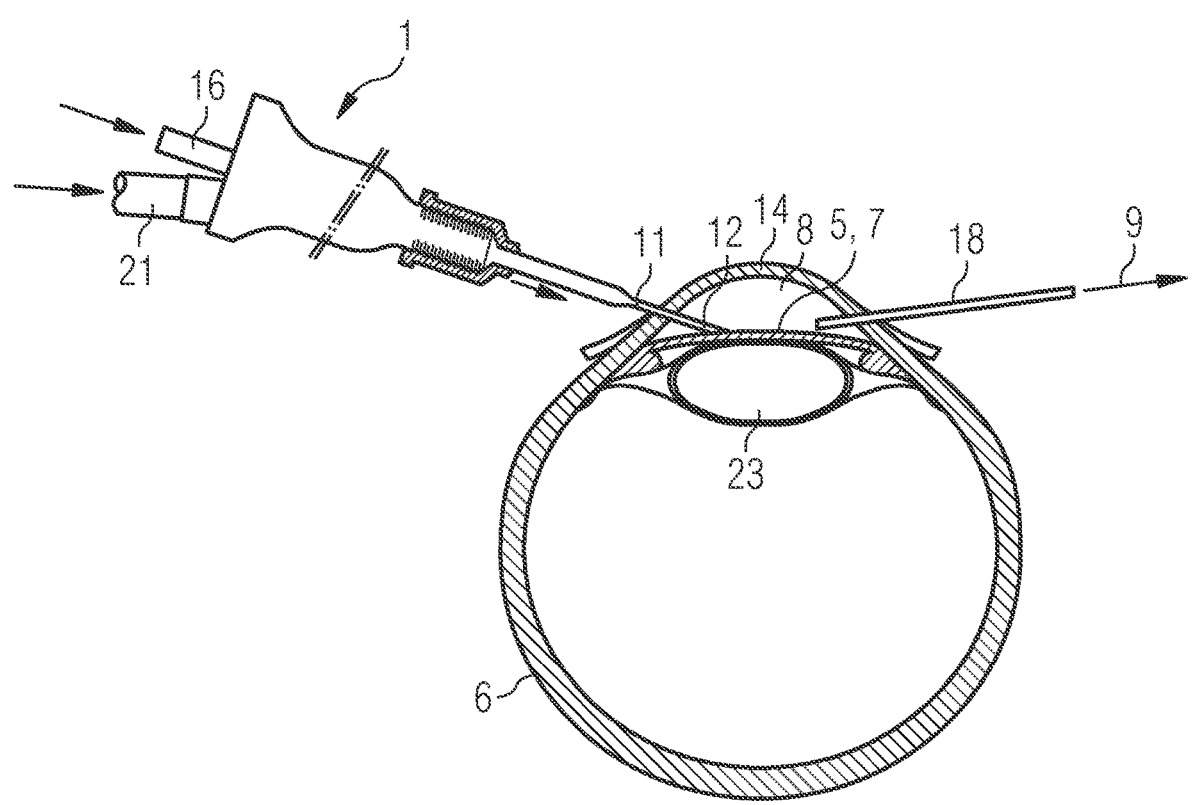
FIG. 2 shows a schematic representation of a human eye together with an applicator device for carrying out the underlying method.

Each of the predefined pressure pulses 2 is generated and applied 102, such that the pressure pulses interact with melanocyte tissue, in particular melanocytes 3 (FIG. 3), of the stroma 4 of the iris 5 of a human or animal eye 6 (FIG. 2).

The pressure pulses 2 are applied in such a way that interaction with the anterior stroma layer 7 of the stroma 4 is such that the melanocytes 3 are ablated, separated or split off, from the anterior stroma layer 7, whilst non-melanocyte tissue of the stroma 4 and anterior stroma layer 7 is left substantially undamaged.

The ablated melanocytes 3 or melanocyte tissue, by the action of the pressure pulses 2, are discharged (in particular: released) into the anterior eye chamber 8 of the eye 6.

In the example embodiment referred to in the flow chart in FIG. 1, the method comprises a further, in particular optional, step of removing 103 ablated melanocyte tissue from the anterior eye chamber 8 by a flow 9 of rinsing fluid 10 generated and/or maintained through/within the anterior eye chamber 8.

The generation of the pressure pulses 2 and the flow 9 of rinsing fluid 10 will be described in more detail in connection with FIG. 2 and FIG. 3 in connection with an example embodiment.

The pressure pulses 2 are generated by means of the applicator device 1, wherein the applicator device 1 comprises a needle-shaped tip 11, which may be entered or pass with a distal end section 12 through a cornea opening 13 provided in the cornea 14 of the eye 6.

The tip 11 comprises an inner channel 15 extending in longitudinal direction of the tip, wherein in the operational mode of the applicator device 1, the inner channel 15 is coupled with a supply line 16 for supplying and guiding the rinsing fluid 10 into and through the inner channel 15, wherein the inner channel 15 leads to a distal opening 17 such that the rinsing fluid 10 can be passed through the inner channel 15 and supplied to the anterior eye chamber 8.

The supply of rinsing fluid 10 to the anterior eye chamber 8 is carried out in such a way that the intraocular fluid pressure is kept in a range between 16 mmHg and 20 mmHg. For this, the anterior eye chamber 8 may be in fluid communication with a drain tube 18 such that the flow 9 of rinsing fluid 10 can be generated within and through the anterior eye chamber 8 by supplying rinsing fluid 10 through the tip end 11 and inner channel 15.

Figure 3:
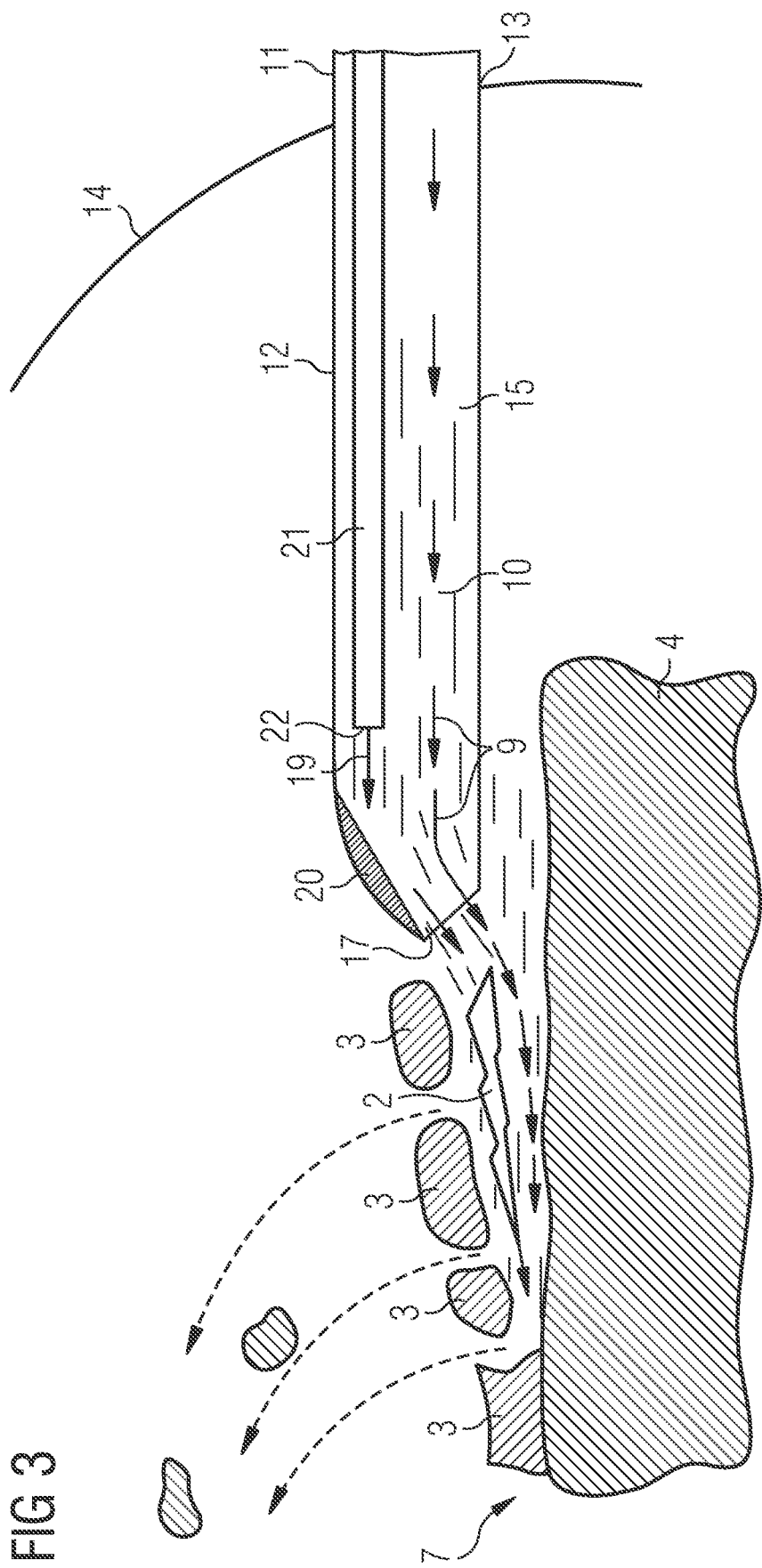
FIG. 3 shows an enlarged view related to FIG. 1.

The flow 9 of rinsing fluid 10 is generated in such a way that melanocyte tissue 3 may be carried away once it is ablated from the anterior stroma layer 7, which is schematically depicted in FIG. 3

The flow 9 of rinsing liquid 10 may be generated as a constant and laminar flow through the anterior eye chamber 8. It shall be noted, that the flow 9 of rinsing fluid 10 may also or in the alternative be generated according to any embodiment as described in further detail above.

Ablation of melanocyte tissue 3 is, as has been discussed, achieved by appropriately applying pressure pulses 2 to the anterior stroma layer 7. The pressure pulses 2 may, for example and as will now be described in connection with the example embodiment shown in FIG. 2 and FIG. 3, be generated by laser-induced cavitation and/or plasma formation/bursts in a fluid medium that is in fluidical communication with the intraocular humoral or fluid contained in the anterior eye chamber 8. The fluid medium may be a mixture of intraocular humoral and rinsing solution 10, or merely rinsing solution 10 in particular as after a certain time of operating the device 1, the intraocular humoral in the anterior eye chamber 8 may be exchanged, or at least greatly exchanged by rinsing solution 10.

In the example embodiment given in connection with FIG. 2 and FIG. 3, laser energy 19 in the form of laser pulses 19 having a defined energy and pulse length, for example as indicated further above, are guided, by means of an optical system to a laser target material 20 located within the inner channel 15. The optical system in the present example comprises an optical fiber 21 that is guided and positioned within the inner channel 15 such that laser pulses 19 fed into the optical fiber 21 may exit the optical fiber 21 at a distal exit face 22 such that the laser pulses 19 impinge on the laser target material 20.

In particular by laser-induced plasma bursts and/or laser induced cavitation generation, pressure pulses 2 are generated in the area of the laser target material 20. As the inner channel 15 is in fluidical communication with the anterior eye chamber 8 by means of the rinsing fluid, the pressure pulses 2 may propagate through the distal exit opening 17 and impinge the anterior stroma layer 7 for ablating melanocyte tissue 3 as described in greater detail above.

The flow 9 of rinsing solution 10 therefore may be considered to have a dual function, namely, a function of removing ablated melanocyte tissue, and a function of enabling pressure pulse propagation to the anterior stroma layer 7 for melanocyte ablation.

The ablation of melanocytes 3 and corresponding melanocyte tissue may, by using the applicator device 1 as referred to in connection with FIG. 2 and FIG. 3, be carried out in accordance with any embodiment as discussed further above. In particular, such embodiments shall apply and may be implemented and incorporated with the exemplary embodiment of FIG. 2 and FIG. 3.

Figure 4:
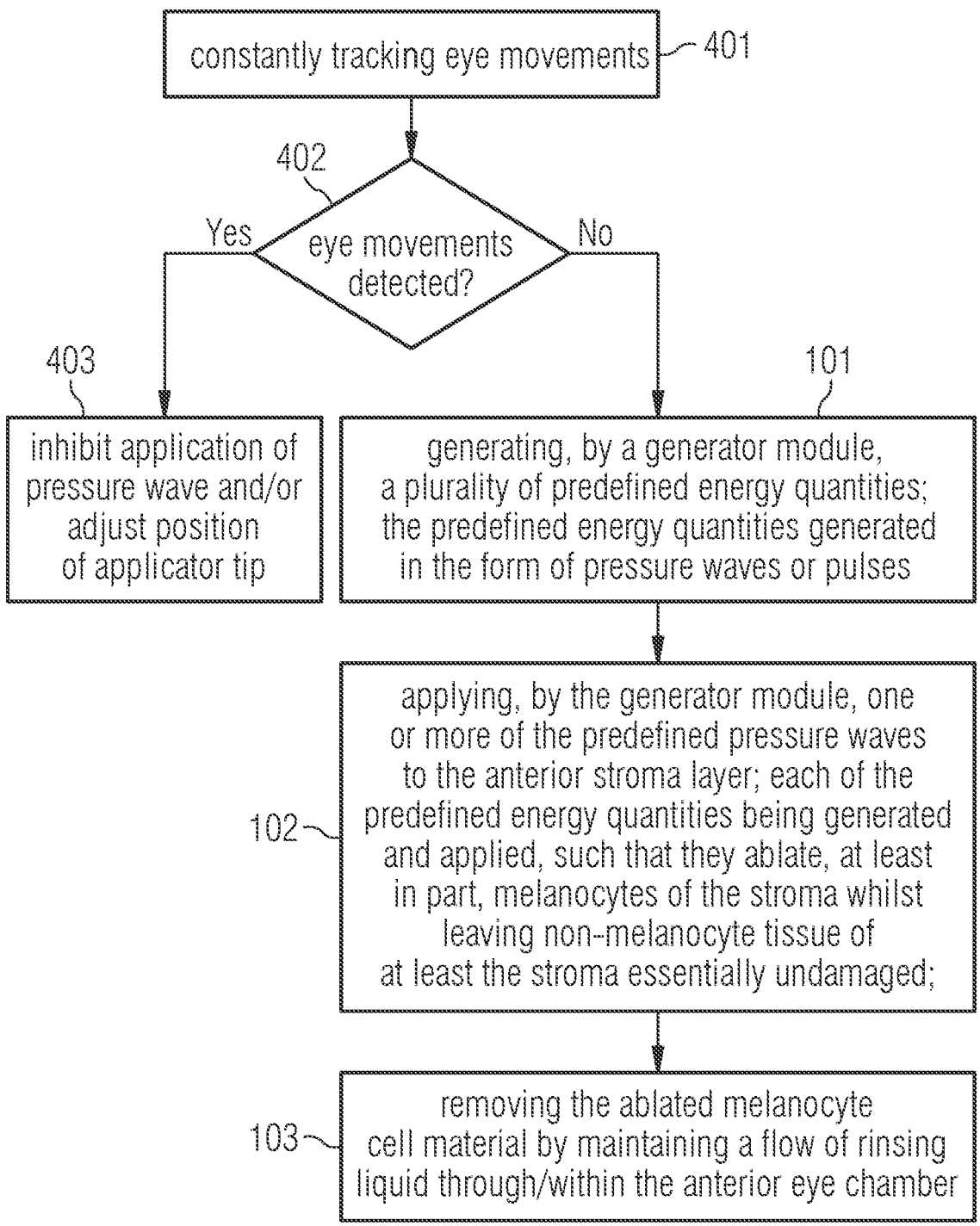
FIG. 4 shows a chart of a modified method as compared to that referred to in FIG. 1.

The method of changing the eye color may further involve a step of tracking 401 one or more components of the eye 6, for example the pupil of the eye 6 as regards eye movements, which is illustrated in FIG. 4 showing a flow chart of such a modified method. The tracking of eye movements may be carried out constantly throughout carrying out the method, wherein in case that a movement of the eye is detected 402, application of pressure pulses may be inhibited and/or cancelled and/or omitted 403, whereas if no movement is detected, the pressure pulses may be generated 101 and applied 102 to anterior stroma layer 8. Further, in case of a detected movement the position of the tip end 11 of the applicator device 1 may, as an option or additionally, be altered so as to compensate the detected eye movement and/or to ensure that emitted pressure pulses 2 hit the anterior stroma layer 4, and not the pupil 23 of the eye 6, for example.

For tracking the eye movement and/or iris movement an eye tracker using a stereoscopic camera system, in particular in connection with infrared light, may be used. The eye tracker may be configured to operate independently from ambient light, or may require specific illumination. The eye tracker, in particular the eye tracking, may involve determining 3D-position of pupil or iris, 3D-viewing direction, pupil size, viewing focus relative to a predefined surface/object.

Figure 5:
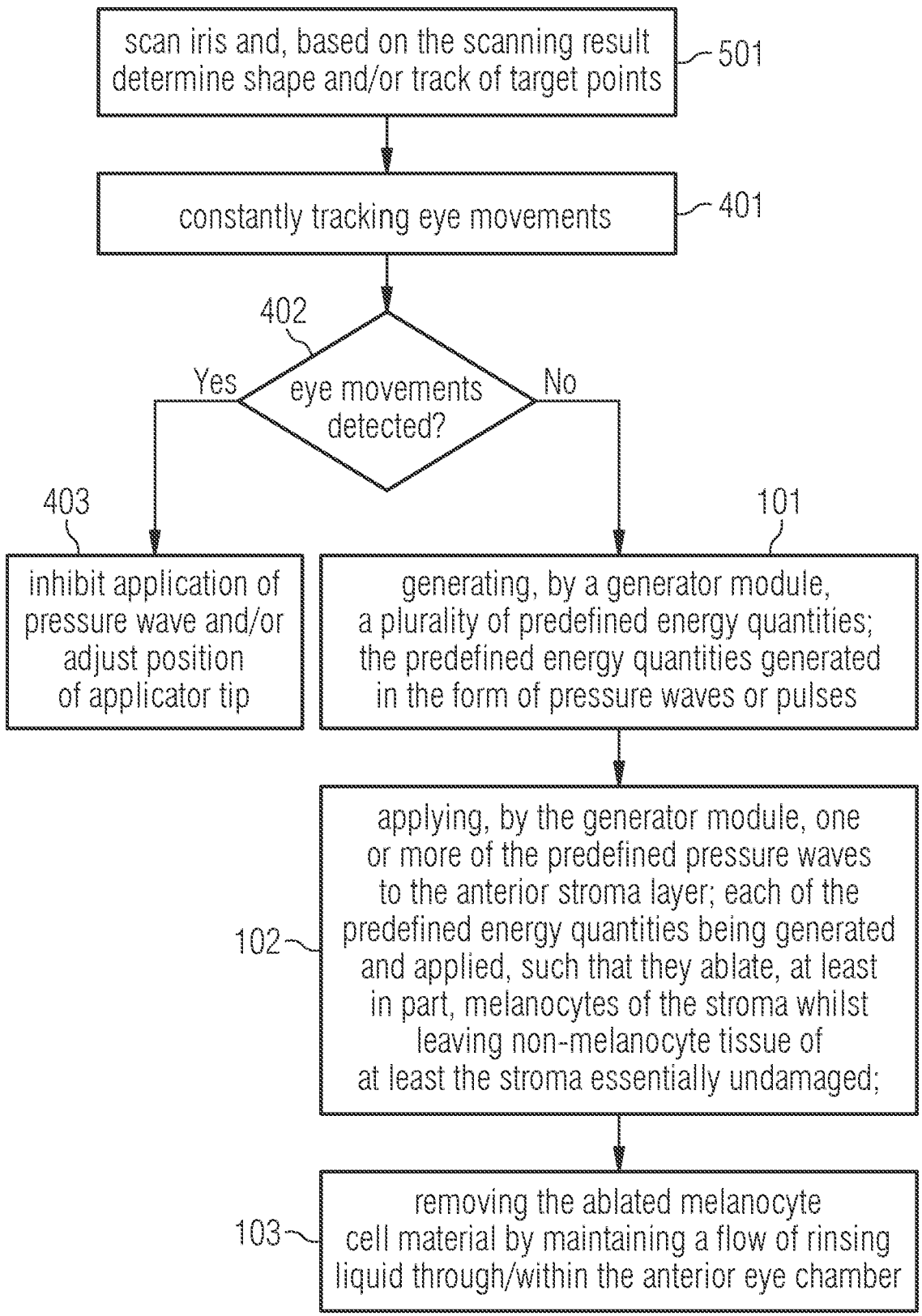
FIG. 5 shows a chart of a further modified method as compared to that referred to in FIG. 4.

FIG. 5 shows a further modified method as compared to the methods of FIG. 1 and FIG. 4, wherein the further modified method involves an additional step of scanning 501 the iris 5 of the eye 6. Based on the scanning result, it is possible for example to determine the shape, e.g. size, of the iris 5, and/or it is possible for example to determine a track or path of target points to be impinged with pressure pulses 2.

In embodiments, the method may involve navigating the tip of the applicator device 1, in particular the distal laser pulse exit opening 17, along the determined track or path so as to ablate melanocyte tissue from the iris 6 along the determined track or path. This may be helpful in automating melanocyte ablation.

In all, it shall become clear from the above discussion, that the method as proposed herein for changing the color of a human's or animal's eye is suitable for solving the underlying problem.

REFERENCE SIGNS 1 applicator device
2 pressure pulse
3 melanocyte
4 stroma
5 iris
6 eye
7 anterior stroma layer
8 anterior eye chamber
9 flow
10 rinsing fluid
11 tip end
12 distal end section
13 cornea opening
14 cornea
15 inner channel
16 supply line
17 distal opening
18 drain tube
19 laser pulse
20 laser target material
21 optical fiber
22 exit face
23 pupil

I claim:
1. A method for changing the human perceptual color appearance of the iris of a human's or animal's eye by selectively decreasing the density of pigments of the anterior stroma layer of the iris, the method comprising:
generating, by a generator module, a plurality of predefined energy quantities, the generator module comprising a laser target and an optical system coupled with a laser source, the optical system adapted for applying laser pulses generated by the laser source to the target to generate the predefined energy quantities in the form of pressure pulses by laser-induced optical breakdown or laser-induced cavitation; and
applying, by the generator module, one or more of the predefined energy quantities to the anterior stroma layer;
each of the predefined energy quantities being generated and applied, such that the energy quantities ablate, at least in part, melanocytes of the anterior stroma layer whilst leaving non-melanocyte tissue of at least the stroma essentially undamaged;
the predefined energy quantities generated and applied to the anterior stroma layer in the form of pressure pulses generated within a fluid medium that is in fluidical communication with the anterior stroma layer;
wherein the pressure pulses are generated to induce a local pressure increase within the fluid medium, the local pressure increase lying between 50 bar and 1,000 bar.

2. The method according to claim 1, wherein the predefined energy quantities are at least in part generated and applied in such a way that ablated tissue or pigment debris, that is generated as an immediate cause of one or more of the applied pressure pulses, is discharged into the anterior eye chamber, such that the discharged tissue can be removed by a mechanically generated flow of rinsing solution through or within the anterior eye chamber.

3. The method according to claim 1, wherein:
the applied pressure pulses or generated pressure pulses, comprise at least one of a pressure current, a pressure wave, and a shock wave propagating in the fluid medium, and in particular having a preferential direction directed towards the anterior stroma layer, or
the applied pressure pulses or generated pressure pulses, involve a pressure jet of the fluid medium generated within the anterior eye chamber and directed under a particular angle of incident towards the anterior stroma layer.

4. The method according to claim 1, wherein at least one of:
the local pressure increase prevails within a distance of 0.3 to 0.7 mm, in particular 0.5 mm, from a point of origin of the pressure pulse; and
the local pressure increase is confined to a cross-sectional area of 0.1 mm$^2$ to 12 mm$^2$ measured in a plane perpendicular to the main propagation direction at a distance of about 5 mm from the point of origin of the pressure pulse.

5. The method according to claim 1, wherein:
the pressure pulses are generated by a shock wave generator device, and
at least one pulse-output region of the shock wave generator device, whilst facing the anterior stroma layer, is moved relative to the iris, preferably at a constant distance to the anterior stroma layer, further preferably in accordance with a predefined pathway along the anterior stroma layer, the relative movement of the pulse-output region being continuous, in particular involving a movement with constant speed, or being dis-continuous, optionally with an intermittent generation of pressure pulses synchronized with the dis-continuous movement, wherein the pulse-output region is optionally provided at a distal end of an applicator element, in particular a handheld applicator element,
the applicator element optionally comprises a needle-shaped extension, and wherein the pulse-output region is provided at a distal end of the needle-shaped extension, and
further optionally, the pulse-output region is defined by an opening at the distal end of the needle-shaped extension, wherein the opening optionally has an opening plane that is tilted at a predefined angle to the longitudinal axis of the needle-shaped extension.

6. The method according to claim 1, wherein:
the pressure pulses are generated with a defined, in particular constant or constantly varying, pulse repetition rate, the pulse repetition rate optionally being adjustable within a pre-specified range by a user via a user interface; and/or
the pulse repetition rate of the pressure pulses is in the range of 1 pulse per second to 10 pulses per second, in particular 10 or 4 or 2 or 1 pulses per second.

7. The method according to claim 1, wherein:
the pressure pulses are generated by the generator module, and the method involving fluidically coupling and/or maintaining a fluidical communication between the pressure-pulse generator unit and the fluid medium, and
the at least one pressure-pulse generator is optionally operated to generate within the fluid medium, or a fluid that is in fluidical communication with the fluid medium a plasma burst and/or cavitation such that at least one plasma-induced pressure pulse is generated within and/or discharged into the fluid medium.

8. The method according to claim 1, further comprising:
irradiating a laser target with laser irradiation thereby generating a shock wave inducing one or more than one pressure pulses by optical breakdown occurring by laser energy being absorbed at a material of the laser target and/or laser-induced cavitation.

9. The method according to claim 8, wherein the irradiating of the laser target further comprises:
generating and applying one or more laser pulses to the laser target material;
wherein the one or more laser pulses are optionally generated to have a pulse duration between 5 ns and 20 ns, preferably 8 ns to 12 ns, and/or a pulse energy between 1 and 20 mJ, preferably between 6 and 15 mJ, in particular in such a way that each laser pulse generates at least one pressure pulse.

10. The method according to claim 1, wherein:
a triggering event for the pressure pulse is generated, in particular by means of a plasma induced by optical breakdown and/or by, in particular laser-induced, cavitation, in an inner channel of a pressure pulse applicator,
the inner channel is filled and/or flushed with fluid medium and/or rinsing solution, and
a fluidical communication between the inner chamber and the anterior eye chamber is established such that a generated pressure pulse is propagated from a source of origin via at least a part of the inner channel through a distal exit opening of the pressure pulse applicator and applied to the target location at the anterior stroma layer.

11. The method according to claim 10, wherein:
the source of origin is located at a laser target provided at an inner wall of the inner channel, preferably at a distal end of the inner channel close to the exit opening,
the triggering event is generated by irradiating the laser target with laser energy so as to generate the one or more pressure pulses by means of an optical breakdown-induced plasma burst and/or laser-induced cavitation within the fluid medium of the inner channel.

12. The method according to claim 11, wherein:
the laser energy is applied to the laser target material by means of an optical fiber at least in part running within the inner cavity; and
the optical fiber has a free end positioned opposite to the laser target material such that laser radiation, in particular laser pulses exiting the optical fiber, is/are directed towards and impinge the laser target.

13. The method according to claim 10, wherein:
a supply flow of fluid medium is generated and maintained through the inner channel into the anterior eye chamber;
a discharge flow of fluid medium is generated and maintained through a drain tube;
the supply flow and discharge flow are generated such that a mean intraocular pressure at least in the anterior eye chamber remains constant while carrying out the method;
the intraocular pressure is kept substantially constant preferably at a value lying in the range between 16 mmHg and 20 mmHg, and
the supply and discharge flow of fluid medium is generated and maintained such that tissue and/or pigment debris generated by melanocyte ablation is removed from the anterior eye chamber via the supply flow and discharge flow of fluid medium.

14. The method of claim 13, further comprising at least one of the following features:
maintaining the supply and discharge flow for a respectively predetermined lapse of time at least during, and/or after applying the one or more pressure pulses to the anterior stroma layer;
maintaining the supply and discharge flow during a predefined lapse of time prior to applying the one or more pressure pulses to the anterior stroma layer;
maintaining the supply and discharge flow for at least one predetermined lapse of time in accordance with a respective, predetermined flow rate profile, the predetermined flow rate profile preferably being constant over time, at least for one, optionally for each, lapse of time, wherein at least one of a start and end point of at least one lapse of time optionally being triggered by the generating, and/or applying the predefined pressure pulse; and
the supply and discharge flow comprise, at least during a predetermined first period of time, a laminar flow, and/or at least during a predetermined second period of time a turbulent flow.

15. The method according to claim 1, comprising the further steps of:
partitioning, preferably based on a captured image of the iris, at least a part of the surface area of the anterior stroma layer into a number of predefined surface sections, preferably having a predetermined size, and/or according to a predefined pathway along the anterior stroma layer for applying the pressure pulses; and
applying a respective number of pressure pulses to one or more surface sections and/or along the predefined pathway;
the predefined surface sections and/or pathway optionally processed in accordance with a predefined succession of surface sections;
the predetermined surface sections, in particular the size of one or more of the predetermined surface sections, and/or the particular succession of surface sections within a processing sequence and/or pathway, and/or an energy content/power of the pulse(s) optionally being determined on the basis of the density of pigments, and/or the specific location of the surface area on the iris, and/or the overall size of the iris;
wherein at least one parameter of the mechanically generated flow is optionally determined on the basis of one or more than one of:
the specific location of a respectively processed surface section and/or pathway,
the particular succession of the surface sections,
the density of pigments,
the size of a respective surface section,
one or more than one parameter related to generating and/or applying the energy quantities.

16. The method according to claim 1, further comprising:
tracking, by an eye movement tracker, in particular an optical tracking module, one or more than one of a position, shape, and movement of the eye or one of the components of the eye, such as the iris or the pupil, relative to a spatial reference point, and
applying, at least in part, the pressure pulses, optionally each of the pressure pulses, in dependence on a tracking result; the method optionally further comprising:
inhibiting the generator module and/or inhibiting application of pressure pulses in case that the tracking result indicates one or more of a change in position, a change in location, a change in shape, and movement, and/or
relocating a target setting for the pressure pulse in accordance with one or more of a change in position, a change in location, a change in shape, and a movement.

17. The method according to claim 1, further comprising:
scanning at least the iris or sections thereof, and/or the anterior eye chamber at least during application of the pressure pulses; and performing one or more than one of the following steps:
storing a scanning result after each predetermined number of applied pressure pulses;
determining, based on the scanning result, an actual location of impingement or an actual averaged location of impingement respectively indicating an actual location on the anterior stroma layer/the iris where one or more pressure pulses indeed impinged on the anterior stroma layer, and optionally tracking the target locations of impingement;
determining a shape of the iris and/or a track, pathway and/or succession of target points to be impinged with the pressure pulses based on the scanning result;
controlling, based on the scanning result, the flow of fluid medium and/or rinsing solution within or through the anterior eye chamber;
based on the scanning result, determining a density of pigments, in particular a local density of pigments, in particular a pigment profile, or at least a parameter representative of the density, in particular the local density, of pigments may be determined based on the scanning result, and controlling the generation and/or application of one or more of the pressure pulses based at least in part on the density of pigments or the respective parameter;

based on the scanning result, determining a change, in particular local change, in the density of pigments, or at least a parameter representative of the change in density of pigments in the anterior stroma layer, and controlling the generation and/or application of the pressure pulses based on the determined change of the density of pigments or the respective parameter;

generating, based on the scanning result, one or more than one display objects for display on a display screen to an operator executing the method; and optionally providing for display on the display screen operational parameters related to the execution of the method, in particular comprising one or more than one of: one or more than one parameter related to the pressure pulses, one or more points of impact of one or more applied pressure pulses on the anterior stroma layer, in particular one or more of a one or more past and future points of impact, of pressure pulses, a first indication representative of a change, in particular local change, of the density of pigments, and a second indication representative of processed, and/or unprocessed surface areas of the anterior surface of the stroma layer.

18. The method according to claim 1, wherein the method further comprises:
a non-surgical treatment of the iris of an eye of a human being or an animal
the treatment modifying the perceived color of the iris by selectively decreasing the density of melanin pigments of the anterior stroma layer of the eye.

19. A computer-readable non-transitory storage medium or controller-unit comprising executable instructions which, when executed on a computer or controller-unit cause the computer or controller-unit to execute a method according to claim 1.

20. A method for changing the human perceptual color appearance of the iris of a human's or animal's eye by selectively decreasing the density of pigments of the anterior stroma layer of the iris, the method comprising:
generating, by a generator module, a plurality of predefined energy quantities, the generator module comprising a laser target and an optical system coupled with a laser source, the optical system adapted for applying laser pulses generated by the laser source to the target to generate the predefined energy quantities in the form of pressure pulses by laser-induced optical breakdown or laser-induced cavitation; and
applying, by the generator module, one or more of the predefined energy quantities to the anterior stroma layer;
each of the predefined energy quantities being generated and applied, such that the energy quantities ablate, at least in part, melanocytes of the stroma whilst leaving non-melanocyte tissue of at least the stroma essentially undamaged;
the predefined energy quantities generated and applied to the anterior stroma layer in the form of pressure pulses generated within a fluid medium that is in fluidical communication with the anterior stroma layer;
the pressure pulses generated by a shock wave generator device, and
at least one pulse-output region of the shock wave generator device, whilst facing the anterior stroma layer, is moved relative to the iris, at a constant distance to the anterior stroma layer, in accordance with a predefined pathway along the anterior stroma layer, the relative movement of the pulse-output region being continuous, in particular involving a movement with constant speed, or being dis-continuous, optionally with an intermittent generation of pressure pulses synchronized with the dis-continuous movement, wherein the pulse-output region is provided at a distal end of a handheld applicator element;
wherein:
the handheld applicator element comprises a needle-shaped extension;
the pulse-output region is provided at a distal end of the needle-shaped extension; and
the pressure pulses are generated to induce a local pressure increase within the fluid medium, the local pressure increase lying between 50 bar and 1,000 bar.

21. A method for changing the human perceptual color appearance of the iris of a human's or animal's eye by selectively decreasing the density of pigments of the anterior stroma layer of the iris, the method comprising:
generating, by a generator module, a plurality of predefined energy quantities, the generator module comprising a laser target and an optical system coupled with a laser source, the optical system adapted for applying laser pulses generated by the laser source to the target to generate the predefined energy quantities in the form of pressure pulses by laser-induced optical breakdown or laser-induced cavitation; and
applying, by the generator module, one or more of the predefined energy quantities to the anterior stroma layer;
each of the predefined energy quantities being generated and applied, such that the energy quantities ablate, at least in part, melanocytes of the anterior stroma layer whilst leaving non-melanocyte tissue of at least the stroma essentially undamaged;
the predefined energy quantities generated and applied to the anterior stroma layer in the form of pressure pulses generated within a fluid medium that is in fluidical communication with the anterior stroma layer;
wherein:
a triggering event for the pressure pulse is generated, in particular by means of a plasma induced by optical breakdown and/or by, in particular laser-induced, cavitation, in an inner channel of a pressure pulse applicator,
the inner channel is filled and/or flushed with fluid medium and/or rinsing solution, and
a fluidical communication between the inner chamber and the anterior eye chamber is established such that a generated pressure pulse is propagated from a source of origin via at least a part of the inner channel through a distal exit opening of the pressure pulse applicator and applied to the target location at the anterior stroma layer.

* * * * *